(12) United States Patent
Baker et al.

(10) Patent No.: US 10,792,174 B2
(45) Date of Patent: *Oct. 6, 2020

(54) BARIATRIC DEVICE AND METHOD

(71) Applicant: BFKW, LLC, Grand Rapids, MI (US)

(72) Inventors: Randal S. Baker, Grand Rapids, MI (US); Paul R. Kemmeter, Ada, MI (US); James A. Foote, Ada, MI (US)

(73) Assignee: BFKW, LLC, Ada, MI (US)

( * ) Notice: Subject to any disclaimer, the term of this patent is extended or adjusted under 35 U.S.C. 154(b) by 288 days.

This patent is subject to a terminal disclaimer.

(21) Appl. No.: 15/805,495

(22) Filed: Nov. 7, 2017

(65) Prior Publication Data

US 2018/0085242 A1  Mar. 29, 2018

Related U.S. Application Data

(63) Continuation of application No. 15/211,034, filed on Jul. 15, 2016, now Pat. No. 9,839,545, which is a
(Continued)

(51) Int. Cl.
*A61F 5/00* (2006.01)
*A61F 2/04* (2013.01)

(52) U.S. Cl.
CPC ............... *A61F 5/004* (2013.01); *A61F 2/04* (2013.01); *A61F 5/0003* (2013.01);
(Continued)

(58) Field of Classification Search
CPC .......... A61F 5/0076; A61F 2/04; A61F 5/003; A61F 5/0079; A61F 5/0036;
(Continued)

(56) References Cited

U.S. PATENT DOCUMENTS

| | | |
|---|---|---|
| 4,403,604 A | 9/1983 | Wilkinson et al. |
| 4,607,618 A | 8/1986 | Angelchik |

(Continued)

FOREIGN PATENT DOCUMENTS

| | | |
|---|---|---|
| EP | 0760696 B1 | 8/2001 |
| EP | 1808888 A2 | 7/2007 |

(Continued)

OTHER PUBLICATIONS

International Search Report of the International Searching Authority from corresponding Patent Cooperation Treaty (PCT) Patent Application No. PCT/US12/38480, dated Jul. 30, 2012.
(Continued)

*Primary Examiner* — Manuel A Mendez
(74) *Attorney, Agent, or Firm* — Gardner Linn

(57) ABSTRACT

A bariatric device and method of causing at least partial satiety in a recipient includes positioning a body in a recipient, the body having a wall defining a lumen, the wall configured to generally conform to the shape and size of the proximal cardiac portion of the stomach. Force is exerted with the wall on the proximal cardiac portion of the stomach in the absence of food thereby activating receptors located in the proximal cardiac portion of the stomach, thereby influencing a neurohormonal feedback mechanism of the recipient to cause at least partial satiety by augmenting fullness caused by food and simulating fullness in the absence of food.

50 Claims, 16 Drawing Sheets

Related U.S. Application Data continuation of application No. 14/920,403, filed on Oct. 22, 2015, now Pat. No. 9,414,948, which is a continuation of application No. 14/314,444, filed on Jun. 25, 2014, now Pat. No. 9,198,789, which is a continuation of application No. 14/142,131, filed on Dec. 27, 2013, now Pat. No. 8,801,599, which is a continuation of application No. 13/331,425, filed on Dec. 20, 2011, now Pat. No. 8,672,831, which is a continuation of application No. 12/915,952, filed on Oct. 29, 2010, now Pat. No. 8,100,931, which is a continuation of application No. 11/463,192, filed on Aug. 8, 2006, now Pat. No. 7,846,174, which is a continuation-in-part of application No. PCT/US2005/036991, filed on Oct. 13, 2005.

(60) Provisional application No. 60/711,310, filed on Aug. 25, 2005, provisional application No. 60/636,845, filed on Dec. 15, 2004, provisional application No. 60/632,147, filed on Dec. 1, 2004, provisional application No. 60/619,308, filed on Oct. 15, 2004.

(52) U.S. Cl.
CPC .......... *A61F 5/0013* (2013.01); *A61F 5/0036* (2013.01); *A61F 5/0043* (2013.01); *A61F 5/0069* (2013.01); *A61F 5/0076* (2013.01); *A61F 5/0089* (2013.01); *A61F 2002/044* (2013.01); *A61F 2002/045* (2013.01)

(58) Field of Classification Search
CPC .... A61F 5/0086; A61F 5/004; A61B 17/1114; A61N 1/36007
See application file for complete search history.

(56) References Cited

U.S. PATENT DOCUMENTS

| | | | |
|---|---|---|---|
| 5,234,454 A | 8/1993 | Bangs | |
| 5,306,300 A | 4/1994 | Berry | |
| 5,366,504 A | 11/1994 | Andersen et al. | |
| 5,507,755 A | 4/1996 | Gresl et al. | |
| 5,662,713 A | 9/1997 | Andersen et al. | |
| 5,741,279 A | 4/1998 | Gordon et al. | |
| 5,820,584 A | 10/1998 | Crabb | |
| 6,146,416 A | 11/2000 | Andersen et al. | |
| 6,264,700 B1 | 7/2001 | Kilcoyne et al. | |
| 6,280,415 B1 | 8/2001 | Johnson | |
| 6,312,437 B1 | 11/2001 | Kortenbach | |
| 6,355,070 B1 | 3/2002 | Andersen et al. | |
| 6,398,802 B1 | 6/2002 | Yee | |
| 6,432,040 B1 | 8/2002 | Meah | |
| 6,447,533 B1 | 9/2002 | Adams | |
| 6,468,298 B1 | 10/2002 | Pelton | |
| 6,544,291 B2 | 4/2003 | Taylor | |
| 6,558,400 B2 | 5/2003 | Deem et al. | |
| 6,572,627 B2 | 6/2003 | Gabbay | |
| 6,656,194 B1 | 12/2003 | Gannoe et al. | |
| 6,675,809 B2 | 1/2004 | Stack et al. | |
| 6,736,828 B1 | 5/2004 | Adams et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,800,081 B2 | 10/2004 | Parodi | |
| 6,802,868 B2 | 10/2004 | Silverman et al. | |
| 6,845,776 B2 | 1/2005 | Stack et al. | |
| 6,916,332 B2 | 7/2005 | Adams | |
| 6,960,233 B1 | 11/2005 | Berg et al. | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,979 B2 | 5/2006 | Silverman et al. | |
| 7,066,945 B2 | 6/2006 | Hashiba et al. | |
| 7,083,629 B2 | 8/2006 | Weller et al. | |
| 7,083,630 B2 | 8/2006 | DeVries et al. | |
| 7,087,088 B2 | 8/2006 | Berg et al. | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,146,984 B2 | 12/2006 | Stack et al. | |
| 7,152,607 B2 | 12/2006 | Stack et al. | |
| 7,211,114 B2 | 5/2007 | Bessler et al. | |
| 7,220,284 B2 | 5/2007 | Kagan et al. | |
| 7,232,461 B2 | 6/2007 | Ramer | |
| 7,347,875 B2 | 3/2008 | Levine et al. | |
| 7,431,725 B2 | 10/2008 | Stack et al. | |
| 7,445,010 B2 | 11/2008 | Kugler et al. | |
| 7,449,024 B2 | 11/2008 | Stafford | |
| 7,682,330 B2 | 3/2010 | Meade et al. | |
| 7,704,264 B2 | 4/2010 | Ewers et al. | |
| 7,708,752 B2 | 5/2010 | Durgin | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,815,591 B2 | 10/2010 | Levine et al. | |
| 7,846,174 B2 * | 12/2010 | Baker ...................... | A61F 2/04 606/191 |
| 7,922,650 B2 | 4/2011 | McWeeney et al. | |
| 7,976,488 B2 | 7/2011 | Levine et al. | |
| 7,981,163 B2 | 7/2011 | Meade et al. | |
| 8,029,455 B2 | 10/2011 | Stack et al. | |
| 8,043,355 B2 | 10/2011 | Shin et al. | |
| 8,100,931 B2 | 1/2012 | Baker et al. | |
| 8,137,301 B2 | 3/2012 | Levine et al. | |
| 8,162,871 B2 | 4/2012 | Levine et al. | |
| 8,282,598 B2 | 10/2012 | Belhe et al. | |
| 8,372,087 B2 | 2/2013 | Baker et al. | |
| 8,447,403 B2 | 5/2013 | Sharma et al. | |
| 8,506,477 B2 | 8/2013 | Waller et al. | |
| 8,529,431 B2 | 9/2013 | Baker et al. | |
| 8,556,956 B2 | 10/2013 | Cully et al. | |
| 8,672,831 B2 | 3/2014 | Baker et al. | |
| 8,721,528 B2 | 5/2014 | Ho et al. | |
| 8,778,011 B2 | 7/2014 | Ryan | |
| 8,784,436 B2 | 7/2014 | Ho et al. | |
| 8,801,599 B2 | 8/2014 | Baker et al. | |
| 8,894,670 B2 | 11/2014 | Baker et al. | |
| 9,055,998 B2 | 6/2015 | Baker | |
| 9,107,742 B2 | 8/2015 | Cully et al. | |
| 9,198,789 B2 | 12/2015 | Baker et al. | |
| 9,375,338 B2 | 6/2016 | Baker et al. | |
| 9,414,948 B2 | 8/2016 | Baker et al. | |
| 9,545,326 B2 | 1/2017 | Baker et al. | |
| 9,549,833 B2 | 1/2017 | McHugo | |
| 9,629,733 B2 | 4/2017 | Roeder et al. | |
| 2001/0020189 A1 | 9/2001 | Taylor | |
| 2002/0032487 A1 | 3/2002 | Dua et al. | |
| 2002/0091395 A1 | 7/2002 | Gabbay | |
| 2003/0040804 A1 | 2/2003 | Stack et al. | |
| 2003/0040808 A1 | 2/2003 | Stack et al. | |
| 2003/0065359 A1 | 4/2003 | Weller et al. | |
| 2003/0109935 A1 | 6/2003 | Geitz | |
| 2003/0199989 A1 | 10/2003 | Stack et al. | |
| 2003/0212450 A1 | 11/2003 | Schlick | |
| 2004/0087976 A1 | 5/2004 | DeVries et al. | |
| 2004/0092892 A1 | 5/2004 | Kagan et al. | |
| 2004/0106987 A1 | 6/2004 | Palasis et al. | |
| 2004/0116999 A1 | 6/2004 | Ledergerber | |
| 2004/0117031 A1 | 6/2004 | Stack et al. | |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0172141 A1 | 9/2004 | Stack et al. | |
| 2004/0210111 A1 | 10/2004 | Okada | |
| 2004/0220682 A1 | 11/2004 | Levine et al. | |
| 2005/0004582 A1 | 1/2005 | Edoga et al. | |

(56) References Cited

U.S. PATENT DOCUMENTS

| | | |
|---|---|---|
| 2005/0043683 A1 | 2/2005 | Ravo |
| 2005/0080395 A1 | 4/2005 | Levine et al. |
| 2005/0096728 A1 | 5/2005 | Ramer |
| 2005/0125020 A1 | 6/2005 | Meade et al. |
| 2005/0197715 A1 | 9/2005 | Kugler et al. |
| 2005/0228504 A1 | 10/2005 | Demarais |
| 2005/0245788 A1 | 11/2005 | Gerber |
| 2005/0245957 A1 | 11/2005 | Starkebaum et al. |
| 2005/0247320 A1 | 11/2005 | Stack et al. |
| 2005/0251165 A1 | 11/2005 | Vaughan et al. |
| 2005/0251176 A1 | 11/2005 | Swanstrom et al. |
| 2005/0283235 A1 | 12/2005 | Kugler et al. |
| 2006/0020277 A1 | 1/2006 | Gostout et al. |
| 2006/0036293 A1 | 2/2006 | Whitehurst et al. |
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0253191 A1 | 11/2006 | Salahieh et al. |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0010875 A1 | 1/2007 | Trout et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208429 A1 | 9/2007 | Leahy |
| 2007/0233221 A1 | 10/2007 | Raju |
| 2007/0260112 A1 | 11/2007 | Rahmani |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1 | 2/2010 | Baker et al. |
| 2010/0063518 A1 | 3/2010 | Baker et al. |
| 2010/0114124 A1 | 5/2010 | Kelleher et al. |
| 2010/0114130 A1 | 5/2010 | Meade et al. |
| 2010/0198237 A1 | 8/2010 | Baker et al. |
| 2010/0256775 A1 | 10/2010 | Belhe et al. |
| 2010/0280313 A1 | 11/2010 | Gasche et al. |
| 2011/0009690 A1 | 1/2011 | Belhe et al. |
| 2011/0092879 A1 | 4/2011 | Baker et al. |
| 2011/0264234 A1 | 10/2011 | Baker et al. |
| 2012/0083871 A1 | 4/2012 | Ryan |
| 2012/0089168 A1 | 4/2012 | Baker et al. |
| 2012/0191213 A1 | 7/2012 | Baker et al. |
| 2012/0191215 A1 | 7/2012 | Baker et al. |
| 2012/0203061 A1 | 8/2012 | Birk |
| 2012/0289991 A1 | 11/2012 | Baker |
| 2012/0310327 A1 | 12/2012 | McHugo |
| 2013/0123811 A1 | 5/2013 | Baker et al. |
| 2013/0296913 A1 | 11/2013 | Foote et al. |
| 2014/0018611 A1 | 1/2014 | Baker et al. |
| 2014/0114230 A1 | 4/2014 | Baker et al. |
| 2014/0121585 A1 | 5/2014 | Baker et al. |
| 2014/0277341 A1 | 9/2014 | Havel et al. |
| 2014/0309681 A1 | 10/2014 | Baker et al. |
| 2015/0025313 A1 | 1/2015 | Baker et al. |
| 2015/0039092 A1 | 2/2015 | Baker et al. |
| 2015/0182239 A1 | 7/2015 | Baker et al. |
| 2016/0038325 A1 | 2/2016 | Baker et al. |
| 2016/0151233 A1 | 6/2016 | Baker et al. |
| 2016/0228268 A1 | 8/2016 | Hingston et al. |
| 2016/0262867 A1 | 9/2016 | Baker et al. |
| 2016/0324671 A1 | 11/2016 | Baker et al. |
| 2017/0172723 A1 | 6/2017 | Foote et al. |

FOREIGN PATENT DOCUMENTS

| | | |
|---|---|---|
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | WO 2011/056608 A1 | 5/2011 |
| WO | WO 2011/063307 A1 | 5/2011 |
| WO | WO 2011/089601 A1 | 7/2011 |
| WO | WO 2011/097209 A1 | 8/2011 |
| WO | WO 2011/116025 A1 | 9/2011 |
| WO | WO 2012/044917 A1 | 4/2012 |
| WO | WO 2012/162114 A1 | 11/2012 |
| WO | WO 2013/090190 A1 | 6/2013 |
| WO | WO 2013/134227 A1 | 9/2013 |
| WO | WO 2014/141239 A1 | 9/2014 |
| WO | WO 2015/031077 A1 | 3/2015 |
| WO | WO 2016/109346 A1 | 7/2016 |

OTHER PUBLICATIONS

International Preliminary Report on Patentability and Written Opinion of the International Searching Authority from corresponding Patent Cooperation Treaty (PCT) Patent Application No. PCT/US12/38480, dated Nov. 29, 2013.

"Obesity: Super-Sized Medical Device Market", Start-Up, Mar. 2003, Technology Strategies (Long Article), pp. 1-10 and a cover page.

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.

(56) References Cited

OTHER PUBLICATIONS

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.

Lowe, Andrew S., M.D. and Sheridan, Maria B., M.D., "Esophageal Stenting," annotated by Israel Patent Office (2004).

Abstract and claims of U.S. Pat. No. 6,960,233 annotated by the Israel Patent Office (Nov. 1, 2005).

Schembre, Drew, "Advances in Esophageal Stenting: the Evolution of Fully Covered Stents for Malignant and Benign Disease," Adv. Ther., Springer Healthcare, Apr. 1, 2010, pp. 1-13.

International Preliminary Report on Patentability and Written Opinion of the International Searching Authority from corresponding Patent Cooperation Treaty (PCT) Patent Application No. PCT/US08/53912, completed Aug. 19, 2009.

International Preliminary Report on Patentability and Written Opinion of the International Searching Authority from corresponding Patent Cooperation Treaty (PCT) Patent Application No. PCT/US05/36991, completed Mar. 6, 2006.

S. Fukudo, T. Nomura, M. Hongo, "Impact of corticotropin-releasing hormone on gastrointestinal motility and adrenocorticotropic hormone in normal controls and patients with irritable bowl syndrome", Jan. 19, 1998.

D.G. Maxton, D.F. Martin, P.J. Whorwell, M. Godfrey. "Abdominal distension in female patients with irritable bowel syndrome: exploration of possible mechanisms", Aug. 3, 1990.

\* cited by examiner

BARIATRIC DEVICE AND METHOD

CROSS REFERENCE TO RELATED APPLICATIONS

The present invention is a continuation of prior application Ser. No. 15/211,034 filed Jul. 15, 2016, now U.S. Pat. No. 9,839,545, which is a continuation of U.S. patent application Ser. No. 14/920,403, filed on Oct. 22, 2015, now U.S. Pat. No. 9,414,948 issued Aug. 16, 2016, which is a continuation of U.S. patent application Ser. No. 14/314,444, filed on Jun. 25, 2014, now U.S. Pat. No. 9,198,789, which is a continuation of U.S. patent application Ser. No. 14/142,131, filed on Dec. 27, 2013, now U.S. Pat. No. 8,801,599, which is a continuation of U.S. patent application Ser. No. 13/331,425 filed on Dec. 20, 2011, now U.S. Pat. No. 8,672,831, which is a continuation of U.S. patent application Ser. No. 12/915,952, filed on Oct. 29, 2010, now U.S. Pat. No. 8,100,931, which is a continuation of U.S. patent application Ser. No. 11/463,192, filed on Aug. 8, 2006, now U.S. Pat. No. 7,846,174, which is continuation-in-part application of International Application No. PCT/US2005/036991, filed on Oct. 13, 2005, entitled BARIATRIC DEVICE AND METHOD, which claims the benefit of 60/619,308 filed on Oct. 15, 2004; and claims the benefit of 60/632,147 filed on Dec. 1, 2004; and claims the benefit of 60/636,845 filed on Dec. 15, 2004; and claims the benefit of 60/711,310 filed on Aug. 25, 2005, the disclosures of which are incorporated herein in their entirety.

BACKGROUND OF THE INVENTION

The present invention is directed to a bariatric device and method of causing at least partial satiety in a patient. In particular, the present invention is directed to a bariatric device and a method of causing at least partial satiety in a patient by a noninvasive or minimally invasive technique.

Obesity is a large and increasing problem in the United States and worldwide. In round numbers, from the period encompassing the year 1990 to the period encompassing the year 2000, the prevalence of overweight people (BMI greater than 25) increased from 56 percent of United States adults to 65 percent and the prevalence of obese adults (BMI greater than 30) increased from 23 percent to 30 percent. Likewise, the prevalence of overweight children and adolescents (ages 6-19 years) increased from 11 percent in the period encompassing the year 1990 to 16 percent in the period encompassing the year 2000. The increasing prevalence of overweight among children and adolescents will make the problem even greater when they reach adulthood. The problem is not limited to the United States. Between 10 percent and 20 percent of European men are obese and between 10 percent and 25 percent of European women are obese. Numerous medical conditions are made worse by obesity including Type II diabetes, stroke, gallbladder disease and various forms of cancer. Approximately 500,000 people in North America and Western Europe are estimated to die from obesity-related diseases every year and obesity is estimated to affect more than one billion adults worldwide. Therefore, there is a pressing and unmet need for a solution to the epidemic problem.

Various techniques are known for reducing obesity in patients. Known techniques tend to be based upon restricting food movement and/or nutrient absorption. One example is gastric bypass surgery on the patient, which is highly invasive. The goal of such surgery is to form a pouch from a portion of the stomach to reduce the volume of the space in the stomach receiving food. When the patient ingests food, the pouch is filled which stretches the stomach wall and produces satiety. One difficulty with such procedure is that it requires food to fill the pouch to create satiety. As a result, dietary restrictions are required for effective operation of the pouch. Such restrictions include withholding of liquids during meals to avoid washing the food from the pouch. Also, liquids with substantial calories tend to pass through the pouch without creating substantial satiety. Moreover, the opening from the pouch tends to become enlarged over time, thus allowing more food to pass while achieving reduced satiety. Thus, patients undergoing such surgical techniques often experience gradual weight gain over time.

Alternative weight loss devices and methods have been proposed. However, such devices and methods may be difficult to place in the patient, have questionable efficacy, and may cause undesirable side effects.

SUMMARY OF THE INVENTION

The present invention utilizes a new principle of implied satiation. The present invention provides a bariatric device and method of causing satiety in a patient that augments the natural response of the body. This may be accomplished using a non-invasive or minimally invasive procedure with a device that may be removable or absorbable. Moreover, satiety may be caused in a manner that does not interfere with other body functions, such as operation of normal reflux mechanism, bile ducts, taking of medications, and the like. The implied satiation technique of the present invention does not rely on either the restrictive or malabsorptive techniques of the prior art.

A bariatric device, according to an aspect of the invention, includes a body having a wall defining a lumen. The wall is configured to generally conform to the shape and size of the proximal cardiac portion of the stomach and to exert pressure on the proximal cardiac portion of the stomach in the absence of food, thereby influencing a neurohormonal feedback mechanism of the patient to cause at least partial satiety by augmenting fullness caused by food and simulating fullness in the absence of food. The lumen is substantially unrestricted. At least one fixation mechanism resists distal migration of the body.

The wall may be made from a self-extendable silicone-coated material. The wall may be flared to thereby conform to the cardiac notch of the proximal cardiac portion of the stomach. The body may be generally frusto-conical in shape. The wall may exert a generally consistent radial pressure on the proximal cardiac portion of the stomach. The wall may be at least partially absorbable.

The fixation system may include barbs, V-shaped appendages, metallic anchors extending radially from said body, staples and/or sutures. The wall may be compressible for deployment through the esophagus. The wall may be removable.

A method of causing at least partial satiety in a recipient, according to an aspect of the invention, includes positioning a body at a proximal cardiac portion of the stomach and fixing the body to the recipient to resist migration of the body. The body has a wall defining a lumen and is configured to the size and shape of the proximal cardiac portion of the stomach. The lumen is substantially unrestricted. Pressure is exerted with the wall on the proximal cardiac portion of the stomach in the absence of food, thereby influencing a neurohormonal feedback mechanism of the patient to cause at least partial satiety by augmenting fullness caused by food and simulating fullness in the absence of food.

Anti-nausea medication may be administered to the recipient at least during initial deployment of said body. Nutritional supplements may be administered to the recipient. The body may be generally frusto-conical in shape. A generally consistent radial pressure may be exerted with the wall to the proximal cardiac portion of the stomach. The wall may be at least partially absorbable.

The fixation system may include barbs, V-shaped appendages, metallic anchors extending radially from said body, staples and/or sutures. The wall may be compressed and the body deployed through a recipient's esophagus. The body may be removed after the recipient has experienced sufficient weight loss.

Thus, it can be seen that embodiments of the present invention provide an implied satietor and implied satiation method that does not require food to generate the satiety through the neurohormonal mechanism of the body. This advantageously produces at least partial satiety in the patient in the absence of food, as well as augmenting fullness caused by food during the ingestion of the food. Moreover, because satiety is not caused by food, the patient would not necessarily need to be subject to dietary restrictions, such as withholding of liquids during meals or withholding of liquids having substantial calories.

Moreover, in contrast to surgical procedures, embodiments of the present invention provide a bariatric device and method of causing at least partial satiety that is minimally invasive and which avoids many of the potential side effects of gastric bypass surgery and other surgical procedures, such as adjustable gastric banding, and the like. Also, because of the placement of the device, there is no interference with operation of gastric functions, such as with the bile ducts, and the like. Further, as previously noted, the bariatric device can be adapted to allow the gastro-esophageal junction to function normally without any significant interference or impediment. Also, embodiments of the invention provide a bariatric device and method of inducing at least partial satiety in the patient that does not operate on the basis of causing flu-like symptoms in the patient in a thwarted effort to attempt to induce the patient to eat less, such as may occur by the placement of devices in the patient's duodenum, or the like.

Additionally, in contrast to pouches formed in gastric bypass surgery, embodiments of the present invention do not include a discharge opening that is subject to enlargement with the passage of time, thereby eliminating at least one source of gradual weight gain in patients undergoing gastric bypass surgery.

Moreover, because it is a non-invasive or minimally invasive procedure, embodiments of the present invention may be applied not only to morbidly obese patients, but also to obese patients, overweight patients, adolescents, and potentially even children.

Thus, it is seen that the present invention is embodied in a bariatric device and method including a body having an expandable wall, which evokes normal neurohormonal responses associated with fullness or satiety. The body wall does so by acting on one or more portions of the distal esophagus and/or the cardia of the patient. The normal filling sensation of the stomach is augmented and amplified. Further, it has been found that the body appears to have a "satiety continuum" where a person transitions from hungry, which is on one end of the continuum or spectrum where there is a lack of satiety, to lacking hunger or being satisfied after eating and to being full with continued consumption. If the person continues to eat to the point of overeating, the person then becomes nauseous, which represents the other end of the continuum. As the pressure applied to the distal esophagus and/or the cardia of a patient is increased, the further along the patient will be on this "continuum" or spectrum. Ideally, then for an extremely overweight person, the bariatric device of the present invention may be best used if sufficient pressure is applied so that the patient is on the nausea end of the spectrum or just below at a "sub-nausea" point.

These and other objects, advantages and features of this invention will become apparent upon review of the following specification in conjunction with the drawings.

DESCRIPTION OF THE PREFERRED EMBODIMENT

Figure 1:
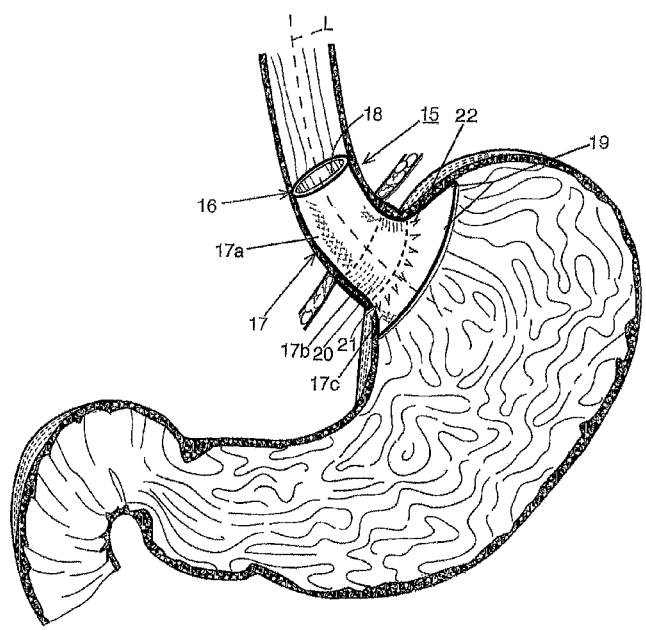
FIG. 1 is a diagram of a bariatric device positioned at the abdominal portion of the esophagus, the esophageal-gastric junction and the proximal cardiac portion of the stomach of the patient.

Referring now specifically to the drawings, and the illustrative embodiments depicted therein, a bariatric device, or implied satietor, 15, which causes satiety by acting on the abdominal portion of the esophagus, and/or the esophageal-gastric junction and/or the proximal cardiac portion of the stomach, is illustrated in FIG. 1 being positioned in the patient. Device 15 includes a body 16 having an expandable wall 17 thereby defining a transverse passage, or lumen 18 through the body. Body 16 is designed to conform to the shape and size of the abdominal portion of the esophagus, the esophageal-gastric junction and/or the proximal cardiac portion, or cardia, of the patient's stomach. The present invention is embodied in various bariatric devices. The devices may be removable, absorbable and/or permanent.

The devices may be manufactured from a synthetic or a bioprosthetic material. While the invention is illustrated with a mesh wall, other configurations are possible, such as coil configurations, and the like. Bariatric device 15 may be positioned utilizing various techniques, such as endoscopic placement with fluoroscopic assist.

Wall 17 is configured to exert an outward pressure, typically a generally radial outward pressure, at the abdominal portion of the esophagus, the esophageal-gastric junction and/or the cardia of the patient. This may be accomplished, for example, by configuring the wall to have a proximal portion 17a to create an interference fit with the abdominal portion of the esophagus and/or a central portion 17b configured to create an interference fit with the esophageal-gastric junction and/or a distal portion 17c configured to create an interference fit with the patient's cardia. The pressure exerted by wall portions 17a, 17b and/or 17c influences the neurohormonal feedback mechanism present at the esophagus and/or stomach to cause at least partial satiety. As will be discussed in more detail below, the pressure exerted by the extendable wall may be fixed or adjustable. The force that influences the neurohormonal feedback mechanism present at the abdominal portion of the esophagus, the esophageal-gastric junction and/or the cardiac portion of the stomach is intended to be relatively consistent over as large an area as reasonably possible. The force exerted by the wall of the bariatric device is believed to activate stretch receptors located in the abdominal portion of the esophagus, the esophageal junction and/or the cardia. In contrast to prior proposed devices, which require that the patient ingest food in order to influence neurohormonal feedback mechanisms, bariatric device 15 simulates fullness in the absence of food. It also augments fullness caused by food.

This interference fit may be created by a self-extendable, or self-expanding, wall. Alternatively, it may be created by an extendable wall, such as a balloon-extendable wall. The extended wall diameter is chosen so that it is somewhat oversized compared to the diameter of the conduit in which it is positioned, namely, the abdominal portion of the esophagus, the esophageal-gastric junction and/or the cardia. A self-extendable wall may be, by way of example, formed from a material, such as metal, fibers or fibrous materials, including carbon fibers, and may be a wall made from a self-extendable silicone-coated material. For example, the wall may be formed from a metal sheet, such as a Nitinol sheet, formed for example, by laser cutting, or from a coil or lattice structure formed from a metal or carbon fiber, which may be encapsulated or embedded in an insert polymer, such as silicone or the like. Alternatively, the wall may be extended by a balloon or fluid extendable reservoir expanding the wall outwardly, including generally radially outwardly, to a position firmly against the wall of the conduit in which the body is inserted. This inflation may be accomplished endoscopically with a blunt needle or with a control as will be discussed in more detail below.

As can be seen in FIG. 1, wall 17 is longitudinally non-symmetrical with respect to the central longitudinal axis "L" defined by the direction of movement of the food along the patient's esophagus and stomach. In particular, as one moves along axis L, the cross-sectional configuration of wall 17 varies proximally to distally. For example, wall portions 17a and 17b are generally cylindrical in shape and wall portion 17c is frusto-conical in shape, flaring outwardly from a distal end of wall portion 17b. Wall portion 17c is angled to conform to the cardiac notch. Wall 17 may also be radially non-symmetrical with respect to this longitudinal axis "L". In particular, certain portions of wall 17 are at a greater radial distance from axis L than portions of the wall at a different location around axis L. For example, wall portion 17c is enlarged at 19 to extend to more of the fundus of the cardia, such as the angle of His. This enlarged portion 19 makes wall 17 radially nonsymmetrical with respect to axis "L".

The narrow portion of lumen 18, which generally is the portion in the patient's esophagus, may have a length that is no longer required to provide enough force to produce satiety. In the illustrative embodiment, the narrow portion of lumen 18 is less than 9 cm in length. In certain embodiments, the narrow portion of lumen 18 is in the range of between 6 cm and 7 cm in length. This reduces the tendency of food to get caught in the lumen as well as any interference with peristalsis of the esophagus while producing force over a sufficient surface area to produce satiety.

In the embodiment illustrated in FIG. 1, bariatric device 15, and corresponding method of causing satiety in a patient, includes providing at least a portion 20 of middle wall portion 17b that does not exert a substantial pressure or force. Such portion may be made from a flaccid material, such as a non-self-expandable material, or may be formed from a plurality of discrete wall portions that simply connect the proximal portion 17a to the distal portion 17c, as more fully described in reference to FIG. 14A below. These discrete wall portions may be interconnected to form a mesh or may be unconnected from each other to simply act as connectors between the proximal portion 17a and the distal portion 17c. The device would be positioned such that the non-self expanding portion 20 covers the gastro-esophageal sphincter. This would allow the anti-reflux mechanism of the gastro-esophageal junction to operate generally normally because the wall of portion 20 would not exert any significant pressure on the sphincter. This embodiment allows the patient to belch, vomit, and the like, while resisting reflux. In bariatric device 15, proximal wall portion 17a is self-expandable and is generally cylindrical in shape to conform to the shape and size of the abdominal portion of the esophagus and distal wall portion 17c is self-expandable and is generally frusto-conically in shape to conform to the shape and size of the proximal cardiac portion of the stomach.

Bariatric device 15 may include a fixation system 21, which is capable of resisting distal migration of the device. Fixation system 21 may include a series of anchors 22 illustrated as a series of V-shaped downwardly directed appendages from wall 17. Alternatively, the anchors may be in the shape of downwardly directed barbs or hooks, metallic anchors extending radially from said body, or the like. Such arrangement provides fixation against migration, typically distal migration, while allowing the device to be easily removed from the patient because the anchors may be configured to provide less resistance to proximal movement. In the embodiment illustrated in FIG. 1, the anchors are positioned at or near the esophageal-gastric junction, such as proximally at distal portion 17c of the wall. This positioning of the anchor takes advantage of the fact that the esophageal gastric junction is thicker and, therefore, stronger at this location.

Figure 2:
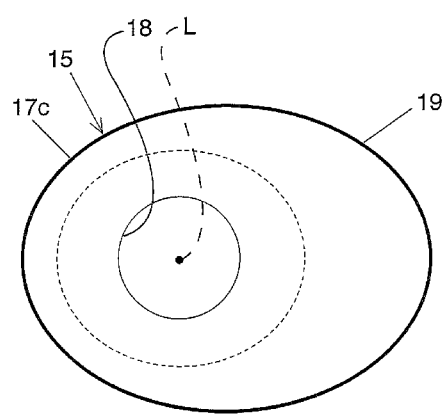
FIG. 2 is a bottom view of the bariatric device in FIG. 1.
Figure 3:
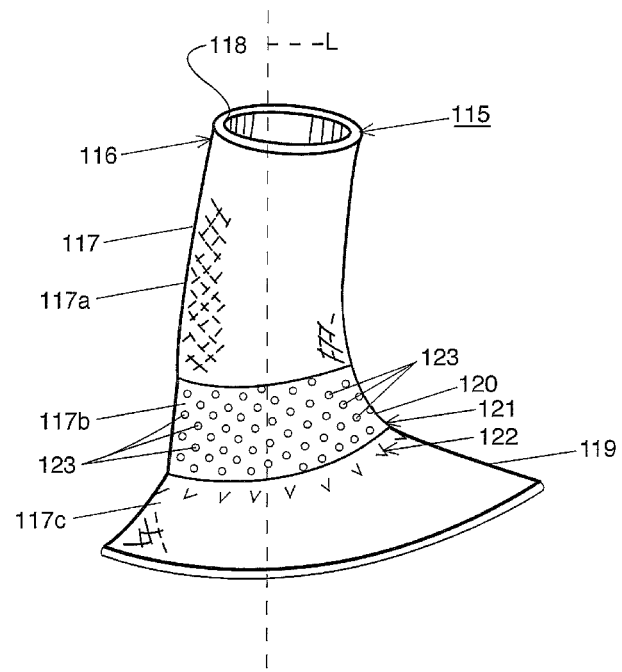
FIG. 3 is a perspective view of an alternative embodiment of the bariatric device in FIG. 1.

A bariatric device 115 includes a wall 117 having a proximal wall portion 117a that applies outward pressure, such as generally radially outward pressure, to the abdominal portion of the esophagus, a distal portion 117c that applies outward pressure, such as generally radially outward pressure, to the proximal cardiac portion of the stomach, and a middle portion 117b that is positioned at the esophageal-gastric junction (FIG. 2). As with bariatric device 15, in bariatric device 115 the central portion 117b is made from a non-expandable material, such as a flaccid material 120. Also, distal portion 117c includes an enlarged portion 119 that extends to more of the function of the cardia, such as the angle of His. Flaccid material 120 includes openings 123 that allow ingrowth of material. Openings 123 define at least in part a fixation system 121. Fixation system 121 may include a secondary, or temporary, means for anchoring bariatric device 115 while allowing tissue to ingrowth through openings 123. Such secondary fixation system may include stitches, staples, or the like. Openings 123 may be sized appropriately to accept such stitches or staples. The sutures could be dissolvable or non-dissolvable. Openings 123 may be as few as, for example, five openings in the flaccid material portion 120. Alternatively, they may be a lattice of small holes that allow tissue ingrowth. The use of tissue ingrowth utilizes the body's reaction to the bariatric device 115 in order to assist in fixing the device against distal migration. Further, the tissue ingrowth, which results from the mucosa essentially incorporating the device into the anatomy of the patient, provides resistance to infection. This ingrowth can be in a portion of the device body or through the entire device body. While some irritation of the mucosa may occur when bariatric device 115 is removed, any such irritation should be relatively minor and readily healed. As with all fixation systems described herein, fixation system 121 may be used in combination with other fixation systems, such as fixation system 21, or the like. Alternately, the tissue ingrowth may be used to promote permanence—in other words to incorporate the device into the body of the patient.

Figure 4:
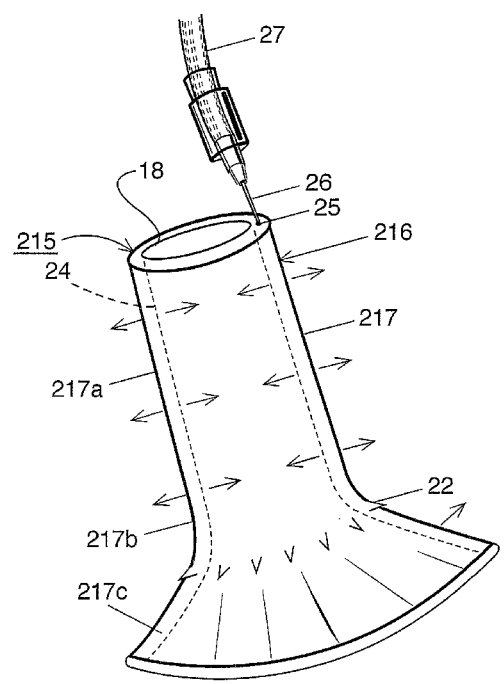
FIG. 4 is the same view as FIG. 3 of another alternative embodiment.
Figure 5:
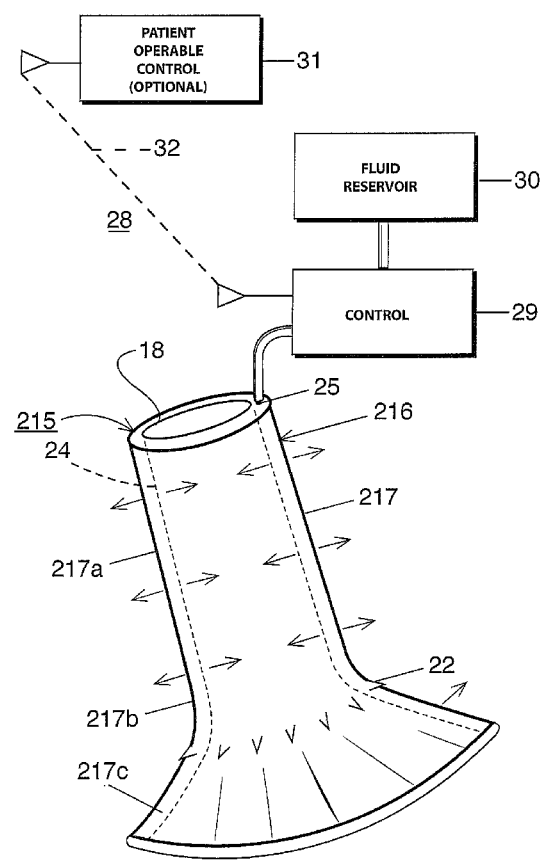
FIG. 5 is the same view as FIG. 4 illustrating an alternative control technique.

An alternative bariatric device 215 includes a body 216 having an expandable wall 217 (FIGS. 4 and 5). Expandable wall 217 defines an internal chamber 24 throughout at least a portion of the proximal portion 217a, middle portion 217b and distal portion 217c of wall 217. Chamber 24 may be a single unitary chamber that extends the length of wall 217 or may be a series of separate chambers that are either interconnected or separated from each other. For example, a chamber may be positioned around proximal portion 217a of wall 217 that is sized and shaped to be positioned at the patient's abdominal esophagus and a chamber may be positioned at distal portion 217c that is sized and shaped to be positioned at the patient's cardia while no chamber is present at all or a portion of 217b that is configured in size to be at the esophageal-gastric junction of the patient. In this manner, wall 217 would not be substantially expandable at the gastro-esophageal sphincter, thereby reducing interference with normal operation of such sphincter, as previously discussed.

As can be seen in FIG. 4, a port 25 may be provided to chamber 24 in order to allow access by a needle 26 connected with a device 27 that is endoscopically inserted in the patient and used to either add fluid to or remove fluid from chamber 24. In this manner, the amount of force exerted by wall 217 may be varied or adjusted. In this manner, for example, a greater amount of force may be applied to a morbidly obese patient, such as one that is more than 40 pounds overweight, while a lower amount of pressure may be applied to patients that are overweight or mildly obese, such as those that are 30 to 40 pounds overweight, for example. Bariatric device 25 is illustrated with a fixation system in the form of anchors 22, although other fixation systems previously described may be utilized. Additionally, distal portion 217c may be radially symmetrical with respect to the longitudinal axis "L" of the device or may be non-symmetrical by including the enlarged portion of distal wall portion 217c as previously described.

As illustrated in FIG. 5, reservoir 24 of bariatric device 215 may, alternatively, be connected with a fluid reservoir 28 positioned within the patient and including a control 29 that is configured to selectively transfer between fluid reservoir 24 in the bariatric device and fluid reservoir 28 in the patient. In this manner, control 29 may control the amount of fluid in fluid chamber 24, thereby adjusting the amount of force exerted by the wall 217 of the device on the conduit in which it is positioned. An optional patient operable control 31 may be provided and interconnected with internal control 29, such as by a radio-frequency link 32, in order to allow a patient or medical attendant to modify the amount of pressure exerted by wall 217.

Control 29 may provide for a temporal adjustment of the amount of pressure exerted by bariatric device 215 on the patient's distal esophagus and/or proximal stomach. By way of example, control 29 may include an algorithm that causes fluid to be transferred from fluid reservoir 30 to fluid chamber 24 of the device 215 in order to increase the amount of pressure, typically radial pressure, exerted by wall 217 during general waking hours of the patient when satiety is desired. Control 29 can further be programmed to transfer fluid from reservoir 24 to reservoir 30 during periods of time when the patient is expected to be sleeping and satiety is not required. Patient control 31 may, alternatively, allow manual adjustment of the amount of force exerted by wall 214 of device 215. For example, when the patient retires at night, the patient may operate user control 31 in order to instruct control 29 to transfer fluid from chamber 24 to fluid reservoir 30, thereby reducing pressure exerted by wall 217. When the patient awakes, the patient may then utilize user control 31 in order to cause control 29 to increase the amount of pressure exerted by wall 217. This temporal control of the amount of force exerted by wall 217 should overcome any potential tachy phylaxis that may result in the diminishing response of the neurohormonal system of the patient to the force exerted by wall 217. Alternatively, the temporal control may be utilized, where appropriate, to adjust the amount of pressure with respect to eating times of the patient, or the like. Control 29 may, alternatively, monitor certain hormonal levels of the patient in order to determine when the patient is expected to eat a meal and may even be a self-learning control system in order to learn the variations in the patient's hormonal levels.

Figure 6:
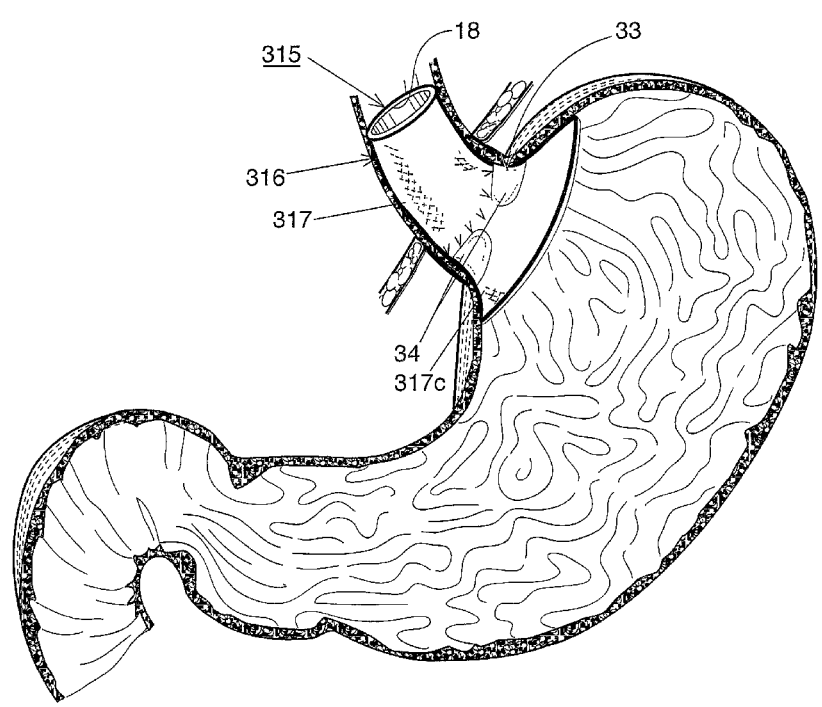
FIG. 6 is the same view as FIG. 2 of yet another alternative embodiment.
Figure 7:
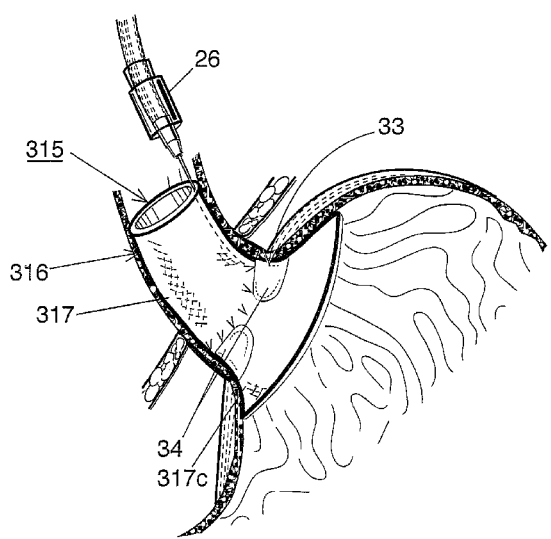
FIG. 7 is the same view as FIG. 6 illustrating adjustment of restriction.

An alternative bariatric device 315 may further include a restriction component 33 restricting discharge of food from lumen 18 (FIG. 6). Restriction component 33 may be in the form of a chamber 34 extending within the lumen of body 316. In the illustrative embodiment, restriction component 33 is adjacent to distal portion 317c of wall 317, but could be at other locations along wall 317. Chamber 34 may be increased or decreased in volume utilizing various techniques, such as by adding or withdrawing a fluid, such as a gas or a liquid, via a blunt needle 26 (FIG. 7). Other known devices, such as an external electronic device that communicates with a control (not shown) and a pump/fluid reservoir within the patient, may be used to adjust the size of restriction component 33. With such configuration, the external control may actuate the pump through the internal control in order to increase or decrease the size of chamber 24. Alternatively, the internal control may be programmed to carry out the adjustment. Chamber 28 restricts the cross-section of lumen 18. Such restriction resists egress from lumen 18 of walls 16 and thereby resists the continued ingestion of food past device 315. This may be useful in patients who tend to continue to eat past satiety.

Figure 8:
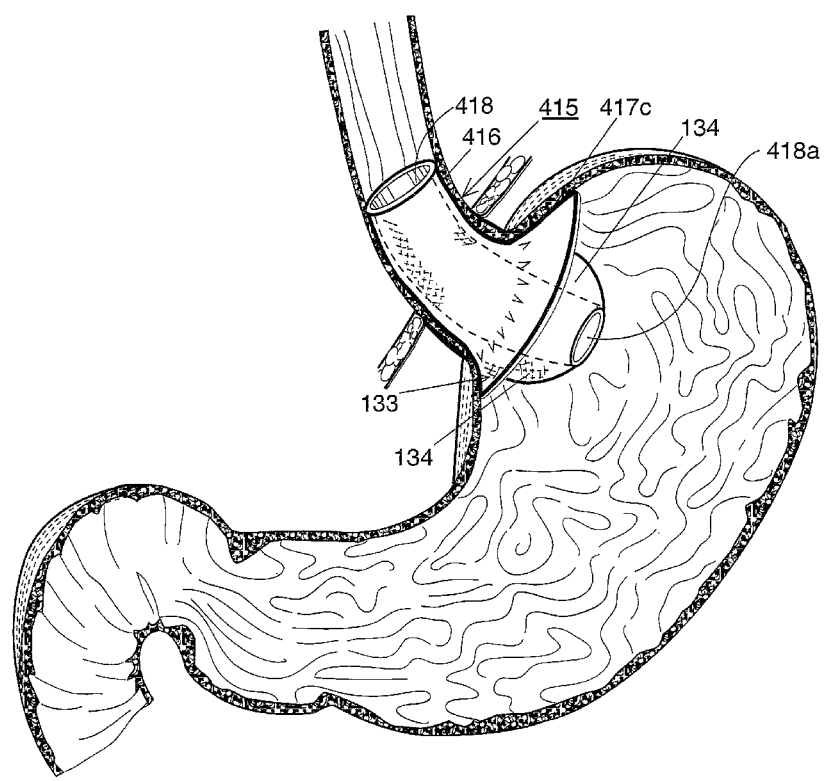
FIG. 8 is the same view as FIG. 2 of yet another alternative embodiment.

FIG. 8 illustrates an alternative bariatric device 415 having a body 416 with a restriction component 133 in the form of an inflatable reservoir or chamber 134, which surrounds the distal portion 418a of the lumen 418. Reservoir 134 provides an adjustable restriction wherein, as additional fluid is added to chamber 134, the increase in the volume of the chamber restricts the diameter of lumen 418 thereby adjusting the ability to resist egress from the lumen of bariatric device 415 thereby providing a variable restriction to ingestion of food. Chamber 134 may also be capable of increasing the external diameter of the device wall 417c thereby placing additional pressure on stretch receptors at the cardia of the patient's stomach.

Figure 9:
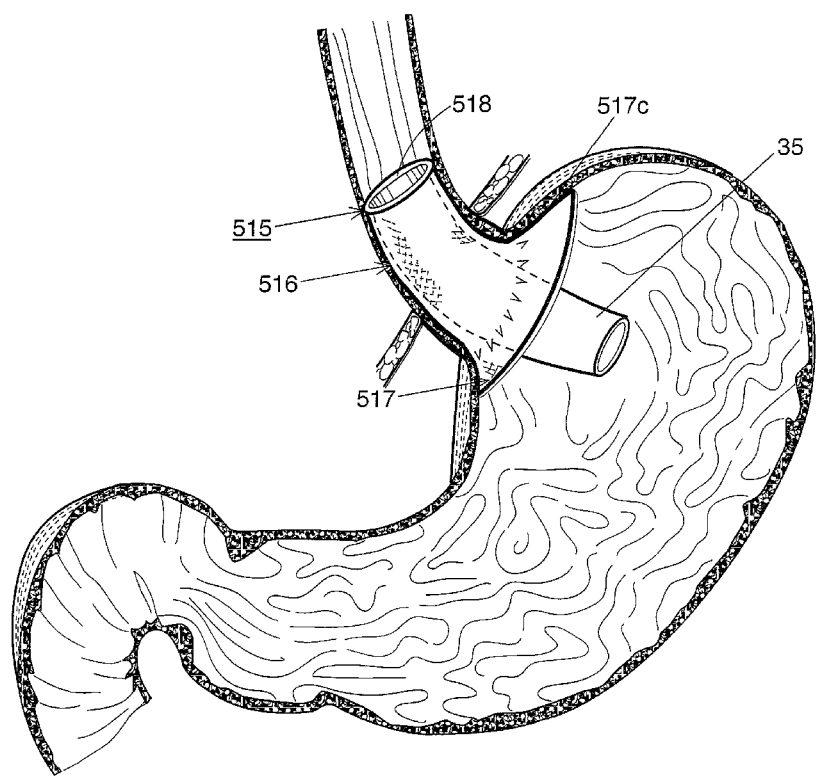
FIG. 9 is the same view as FIG. 2 of yet another alternative embodiment.

An alternative bariatric device 515 may include a body 516 having a wall 517 including an anti-reflux component 35 (FIG. 9). Anti-reflux component 35 may be in the form of a one-way valve in order to resist reflux from the stomach to the esophagus. As best seen in FIG. 9, anti-reflux component 35 may be in the form of a tubular extension of lumen 518 that expands to allow distal movement of food but collapses to reduce reflux.

Figure 10:
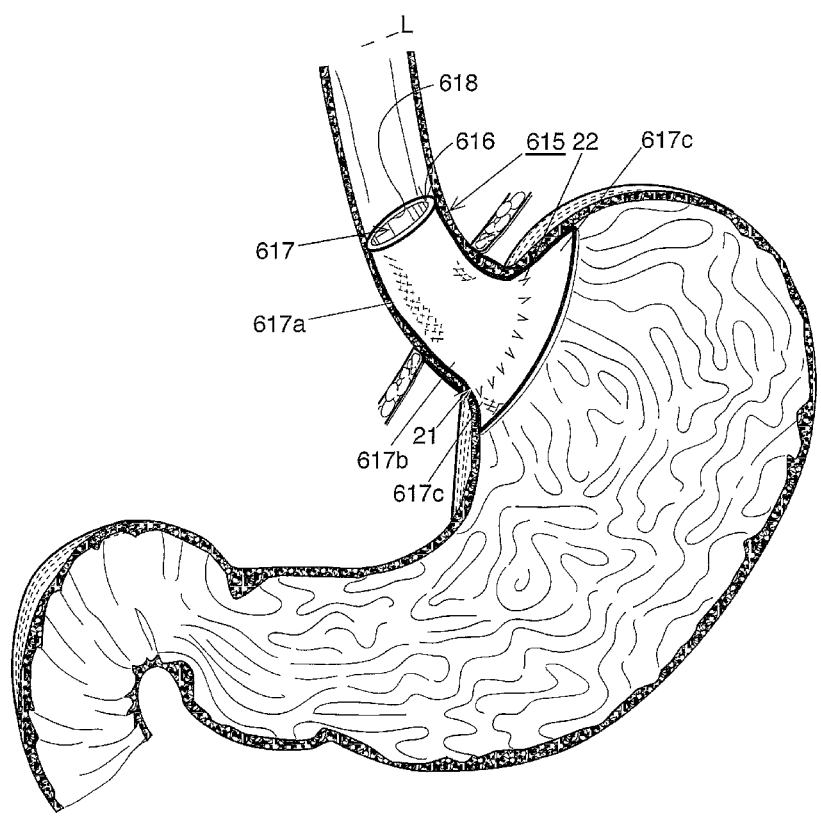
FIG. 10 is the same view as FIG. 1 of yet another alternative embodiment.

An alternative bariatric device 615 includes a body 616 having a wall 617 that is self-expandable at a proximal portion 617a, a middle portion 617b and a distal portion 617c, the latter being configured to the cardiac notch of the patient (FIG. 10). Bariatric device 615 includes a fixation system 21, such as a series of anchors 22, at the esophageal-gastric junction of the patient. The entire surface of wall 617 is made of a self-expanding material.

Figure 11:
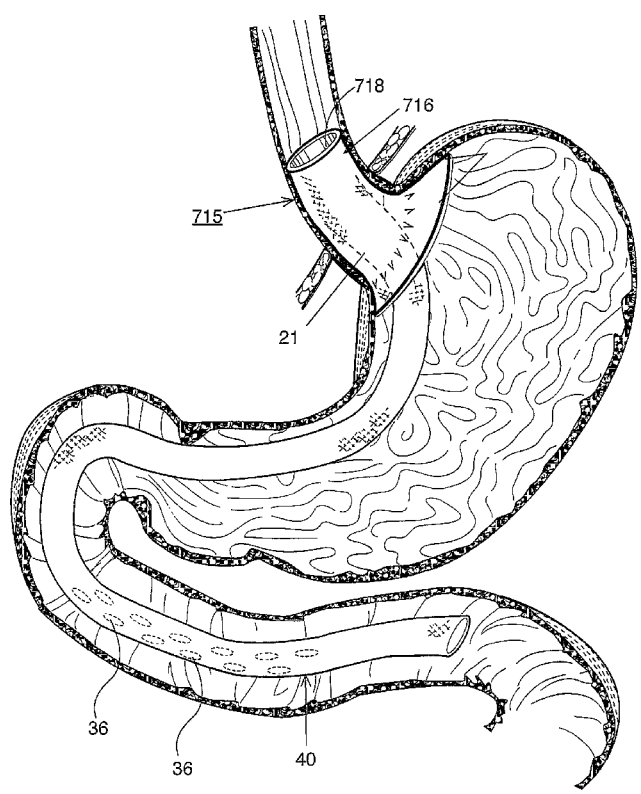
FIG. 11 is the same view as FIG. 1 of yet another alternative embodiment.

An alternative bariatric device 715 illustrated in FIG. 11 has a body 716 in which egress from the lumen 718 is from a discharge portion 40 of the device located at or near the patient's intestines. This provides additional weight loss by substantially bypassing the patient's stomach and discharging to the intestines. Device 715 may include a series of perforations 36 at discharge portion 40 in order to distribute the egress from lumen 718 along the small intestine of the patient. Use of bariatric device 715 may require dietary restrictions to avoid food collection in the elongated lumen.

Figure 12:
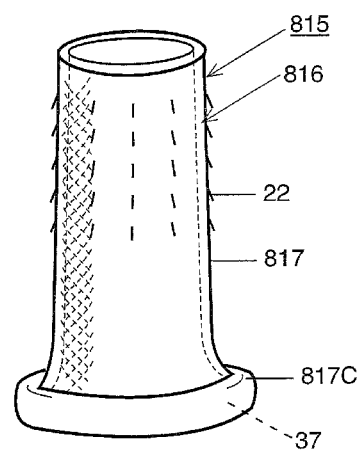
FIG. 12 is the same view as FIG. 2 of yet another alternative embodiment.
Figure 13:
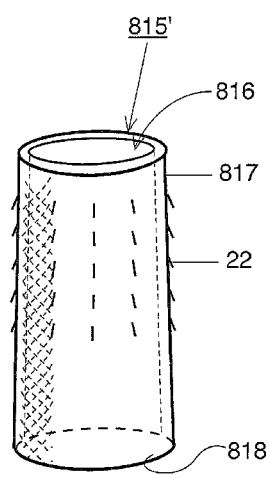
FIG. 13 is the same view as FIG. 2 of yet another alternative embodiment.

Anchors may be positioned at various locations along the exterior of the wall of the device. For an example, an alternative bariatric device 815 is illustrated in FIG. 12 with a body 816 having a wall 817 having anchors, such as V-shaped appendages, barbs, or hooks distributed along the outer wall of the body. The fixation system may also be in the form of a balloon-expandable wall 817c defining a chamber 37 that applies sufficient pressure on the conduit in which the device is located in order to resist distal migration of the device. The balloon can extend the device wall to produce fixation and can be deflated in order to allow the device to be removed. FIG. 13 illustrates an alternative bariatric device 815' having a body 816 with a wall 817 defining a lumen 818 without a chamber. Other fixation systems may be apparent to the skilled artisan, such as stitching, stapling, and the like.

Figure 14:
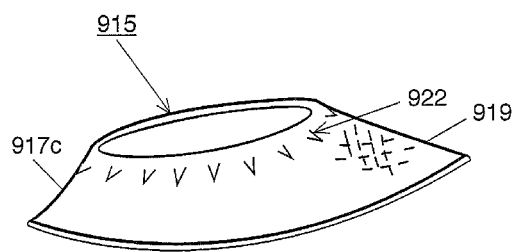
FIG. 14 is the same view as FIG. 2 of yet another alternative embodiment.

An alternative bariatric device 915 illustrated in FIG. 14 includes a body 916 having a wall 917 that is positioned virtually entirely within the patient's stomach. Wall 917 is of a size and shape to conform to the cardiac portion of the stomach, cardia, and is configured to exert pressure, typically radial pressure, on the cardia. Device 915 includes a fixation system 922 that engages the cardia or the esophageal-gastric junction.

Figure 14A:
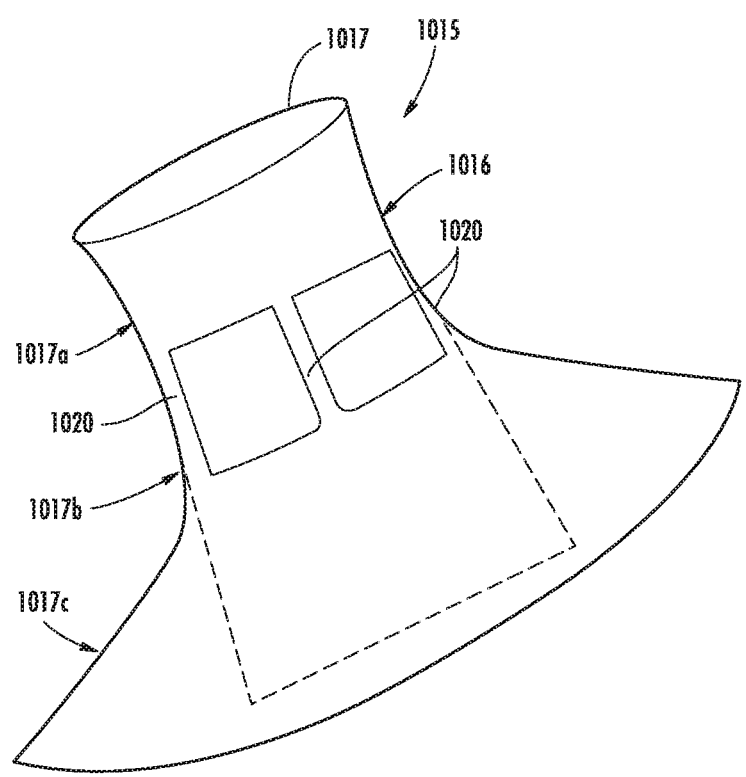
FIG. 14A is a perspective view of an alternate embodiment of the bariatric device of FIG. 1.

As noted above, the non-self-expanding portion of bariatric device of the present invention may be formed from discrete wall portions. Referring to FIG. 14A, device 1015 is of similar construction to device 15 and includes a body 1016 having an expandable wall 1017, which defines a lumen 1018. Wall 1017 is similar to wall 17 and includes a proximal portion 1017a to exert pressure on the abdominal portion of the esophagus and a distal portion 1017c that is configured to exert pressure on the cardia. For further details of portions 1017a and 1017c reference is made to the previous embodiments.

In the illustrated embodiment, the central portion 1017b of the body 1016 is formed from discrete wall portions 1020, which connect the proximal and distal portions 1017a, 1017c of wall 1017 together. Wall portions 1020 may act as tension members between the distal portion and the proximal portion and may further act as compression members to maintain the distal and proximal portions at a desired spacing, but which do not exert any significant outward or radial pressure on the gastro-esophageal junction. Wall portions 1020 may be generally equal in size and evenly spaced around the perimeter of body 1016 or may be unevenly spaced and, further, may have different widths and lengths. For example, the lengths of the wall portions may fall in a range of 0.75 cm to 1.5 cm. The number of wall portions may vary, with the illustrated embodiment depicting four wall portions that are generally evenly spaced around the perimeter of body 1016.

As noted above, wall portions 1020 optionally form a non-self-expanding portion of wall 1017 and align with the gastro-esophageal junction to allow the junction to function normally. The spaces between the wall portions 1020 may comprise holes or openings or may be filled by a flexible membrane or flaccid material.

In addition, wall portions 1020 may provide fixation points, for example, for sutures to secure device 1015 at or near the gastro-esophageal junction in which case the material forming wall portions 1020 may formed from a relatively stiff material, such as fibers or fibrous material, for example, embedded in silicone, for example.

Further, the upper open end or entrance of body 1016 may be flared outwardly to bear or seal against the esophageal wall to essentially close off the space or gap between device 1015 and the esophagus.

Various delivery systems may be utilized to deliver any of the bariatric devices 15-1015 to the patient. Such a delivery system may include a tube device (not shown) into which the bariatric device is compressed. The tube device may be a stiff or flexible tube and be sized and shaped to easily fit within the patient's esophagus. Such a delivery system includes a deployment mechanism (not shown) to retract the bariatric device from the tube. As the bariatric device is removed from the tube, it assumes its expanded form. If a self-expanding wall is utilized, the bariatric device will assert pressure, such as a generally radial pressure, on the distal esophagus and/or the cardia of the patient when removed from the tube. If an expandable wall is utilized, such as a bladder, the bladder is inflated in order to exert pressure. Various markers, such as fluorescent markers, may be applied to the wall of the bariatric device in order to allow for fluoroscopic assist in the placement of the device.

Figure 15:
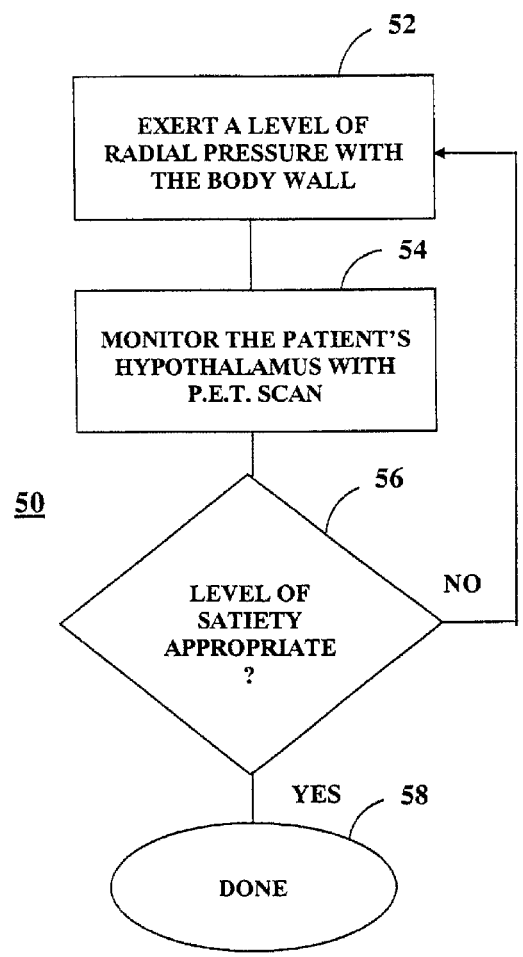
FIG. 15 is a block diagram of a technique for selecting the level of pressure exerted by the body wall.

A method 50 may be provided for monitoring and, if desired, adjusting the amount of satiety produced by the bariatric device and method (FIG. 15). In method 50, a bariatric device 15-1015 is inserted in the patient at 52 and a level of pressure, such as generally radial pressure, is applied by the body wall of the device. The level of satiety is monitored, such as by monitoring the patient's hypothalamus at 54, such as with a Positron Emission Tomography (P.E.T.) scan. The P.E.T. scan produces a visual image of the hypothalamus that changes colors with the amount of activity of the hypothalamus. By observing the color of the hypothalamus through the P.E.T. scan, a determination is made at 56 whether an appropriate level of satiety is obtained. If it is, then the procedure is done at 58.

If it is determined at 56 that an appropriate level of satiety is not being obtained, the process returns to 52 where a different level of pressure may be adjusted by the body. The adjustment of pressure may be in the form of adding or subtracting fluid from a bariatric device having an expandable wall by the use of a chamber 24. Alternatively, the adjustment of the pressure may be in the form of deploying a different size or characteristic device, which is self-expandable and applies a different force to the patient through the self-expandable wall. The amount of satiety may be different for different patients. For example, a patient who is overweight may require a particular level of pressure, whereas a more obese, such as a morbidly obese, patient may require a higher level of satiety. Likewise, a child or an adolescent may require different levels of pressure. The ability to obtain immediate feedback on satiety strength allows the efficacy of the system to be established at deployment rather than monitoring the patient for weight loss and adjusting it after the patient has lost either too much or too little weight.

Alternately, the amount of satiety can be gauged by where the patient falls on the satiety continuum—that is whether they are hungry, satisfied, full or even nauseous. For a morbidly obese person, it may be desirable to apply sufficient pressure so that the patient is nauseous and then optionally reduced slightly so that the patient just below being nauseated or at a sub-nauseous level. This may be particularly useful when a remote control is being used in combination with an adjustable device where the patient may themselves adjust the level of pressure to maintain their desired or a prescribed level of satiety.

Any of the bariatric devices 15-1015 may be used as part of a multi-disciplinary comprehensive program. This may include the adjustment of medications as the patient experiences weight loss. For example, for patients taking diabetic medications, less insulin may be required as a patient loses weight. Also, blood pressure medications and other medications may be adjusted as the patient loses weight.

Because of the ability of the bariatric device 15-1015 to cause satiety, it is possible, in certain patients, that the patient will require nutritional supplements, such as protein liquids, in order to ensure adequate nutritional needs, such as protein intake. Also, anti-nausea medications may be given to the patient, especially at the beginning of the placement. This is because a bariatric device, according to the invention, may cause nausea at the beginning of the placement.

In order to reduce the likelihood of food getting caught in the lumen and in order to minimize interference with natural peristalsis in the esophagus, the length of the lumen is generally kept below 9 cm. In most embodiments, the length of the lumen is in the range of approximately 6 cm to approximately 7 cm. Widened portions of the body, such as distal portions 17c-1017c, are not considered part of the lumen for determining the length of the lumen. The expandable wall, whether self-expanding or balloon-expandable, should provide consistent pressure over as large an area as possible in order to induce adequate satiety, consistent with an effort to keep the lumen as short as possible.

Thus, it is seen that the present invention introduces a new category of weight loss techniques: implied satiation. The invention advantageously utilizes stretch receptors, such as those located at the abdominal portion of the esophagus and/or esophageal-gastric junction and/or the cardiac portion of the stomach of the patient to cause satiety. In contrast to gastric bypass surgery and adjustable gastric bands, the present invention does not require surgical intervention. In that regard, the present invention provides a non-invasive or minimally invasive alternative. However, the invention may be utilized in combination with known restrictive and/or malabsorptive techniques, such as gastric bypass surgery and adjustable gastric bands to further help the patient lose weight. Advantageously, the present invention may be applied to patients who are contraindicated for surgery, such as those with mildly high obesity and for those at risk for surgery. Also, the invention may be used to achieve sufficient weight loss in morbidly obese patients to stabilize the patient for gastric bypass surgery. Moreover, the present invention may be properly sized for use with children and adolescence. Thus, the present invention provides a non-intrusive or minimally intrusive technique for addressing the increasing epidemic of obesity in adolescents and children, as well as adults.

The present invention also comprehends an implied satietor that is capable of exerting pressure at the patient's abdominal portion of the esophagus, esophageal-gastric junction and/or cardia, such as by suitable dimensioning of a self-expanding wall or by a mechanism for expanding the wall outwardly. Examples of such a mechanism may be a bladder mechanism whereby the wall could exert varying pressures. The present invention also has the capability of assisting in reducing esophageal leakage. This may further enhance the use of the invention in combination with other techniques, such as gastric bypass surgery, esophageal tumors, and the like. In addition to influencing the neurohormonal feedback mechanism present at the abdominal portion of the esophagus, the present invention is capable of resisting egress from the lumen of the satiety device. This provides additional benefit to certain patients by resisting their ability to ingest food beyond satiety. Because the device may be inserted endoscopically with fluoroscopic assist, the device may be suitably and accurately positioned at the desired location within the patient's esophagus, esophageal-gastric junction and/or cardia and adjustments made to the satiety device as required. Moreover, the device may be subsequently removed from the patient if indicated. The use of various fixation systems allow the device to be positioned at or near the abdominal portion of the esophagus, the esophageal-gastric junction and/or the cardia while resisting distal migration of the device. Moreover, the use of such fixation system may allow for the satiety device to be readily removed from the patient.

Evidence of the viability of the invention can be seen by its principle having been reduced to practice and found to cause weight loss in patients. The patients, who ranged from non-obese to morbidly obese, lost weight, generally over a one or two week period during which the device was in place. The patients experienced some initial nausea. They reported satiety throughout placement of the device. When the device was no longer present, the patients regained hunger.

Changes and modifications in the specifically described embodiments can be carried out without departing from the principles of the invention, which is intended to be limited only by the scope of the appended claims, as interpreted according to the principles of patent law including the doctrine of equivalents.

The embodiments of the invention in which an exclusive property or privilege is claimed are defined as follows:

1. An intraluminal device adapted to be deployed in a recipient having a gastro-intestinal (GI) tract comprising an esophagus, a stomach with a cardiac portion and an esophageal gastric (EG) junction having a sphincter between the esophagus and the cardiac portion of the stomach, the intraluminal device comprising:
   a body having a wall defining a lumen, said wall having at least one selected from (i) an esophageal wall portion configured to generally conform to the shape and size of the abdominal portion of the esophagus (ii) an EG wall portion that is sized to generally conform to the size and shape of the EG junction and (iii) a cardiac wall portion that is sized to generally conform to the size and shape of the cardiac portion of the stomach;
   said wall adapted to exert force in the absence of food to a portion of the GI tract of the recipient to thereby influence a neurohormonal feedback mechanism of the recipient to cause at least partial satiety by augmenting fullness caused by food and simulating fullness in the absence of food; and
   a fixation system at an outer surface of said wall that is adapted to resist distal migration of said body, said fixation system comprising a plurality of anchors comprising at least one chosen from distally directed appendages, distally directed barbs and distally directed hooks.

2. The intraluminal device as claimed in claim 1 wherein said wall has said EG wall portion and said cardiac wall portion, wherein said cardiac wall portion is adapted to exert force at least on the cardiac portion of the stomach.

3. The intraluminal device as claimed in claim 2 wherein said EG wall portion is adapted to not exert a substantial force at the EG junction of the recipient in order to allow the sphincter of the EG junction of the recipient to operate generally normally.

4. The intraluminal device as claimed in claim 3 wherein said EG wall portion comprises a plurality of spaced apart tension members between the esophageal wall portion and the cardiac wall portion.

5. The intraluminal device as claimed in claim 1 wherein said wall is adapted to exert a generally constant force on the portion of the GI tract.

6. The intraluminal device as claimed in any of claim 1 wherein said wall is adapted to exert an adjustable force on the portion of the GI tract.

7. The intraluminal device as claimed in claim 6 including a control, said control is adapted to controlling an amount of force exerted by said wall on the portion of the GI tract.

8. The intraluminal device as claimed in claim 7 wherein said control is adapted to temporally adjust an amount of force exerted by said wall on the portion of the GI tract.

9. The intraluminal device as claimed in claim 1 wherein said fixation system includes a tissue ingrowth portion of said body that is adapted to facilitate tissue ingrowth.

10. The intraluminal device as claimed in claim 9 wherein said plurality of anchors are adapted to resist distal migration of said body while tissue grows into said tissue ingrowth portion.

11. The intraluminal device as claimed in claim 1 wherein said wall is made at least in part of an absorbable material.

12. The intraluminal device as claimed in claim 1 wherein said anchors are distributed about said outer surface of said esophageal wall portion.

13. An intraluminal device adapted to be deployed in a recipient having a gastro-intestinal (GI) tract comprising an esophagus, a stomach with a cardiac portion and a esophageal gastric (EG) junction having a sphincter between the esophagus and the cardiac portion of the stomach, the intraluminal device comprising:
   a body having a wall defining a lumen, said wall having at least one selected from (i) an esophageal wall portion configured to generally conform to the shape and size of the abdominal portion of the esophagus (ii) an EG wall portion that is sized to generally conform to the size and shape of the EG junction and (iii) a cardiac wall portion that is sized to generally conform to the size and shape of the cardiac portion of the stomach;
   said wall adapted to exert force in the absence of food to a portion of the GI tract of the recipient to thereby influence a neurohormonal feedback mechanism of the recipient to cause at least partial satiety by augmenting fullness caused by food and simulating fullness in the absence of food; and
   a fixation system at an outer surface of said wall that is adapted to resist distal migration of said body, said fixation system comprising a plurality of anchors that are configured to provide less resistance to proximal movement of said body than to distal movement of said body.

14. The intraluminal device as claimed in claim 13 wherein said wall has said EG wall portion and said cardiac wall portion, wherein said cardiac wall portion is adapted to exert force at least on the cardiac portion of the stomach.

15. The intraluminal device as claimed in claim 14 wherein said EG wall portion is adapted to not exert a substantial force on the EG junction of the recipient in order to allow the sphincter of the EG junction of the recipient to operate generally normally.

16. The intraluminal device as claimed in claim 15 wherein said EG wall portion comprises a plurality of spaced apart tension members between the esophageal wall portion and the cardiac wall portion.

17. The intraluminal device as claimed in claim 13 wherein said wall is adapted to exert a generally constant force on the portion of the GI tract.

18. The intraluminal device as claimed in any of claim 13 wherein said wall is adapted to exert an adjustable force on the portion of the GI tract.

19. The intraluminal device as claimed in claim 18 including a control, said control is adapted to controlling an amount of force exerted by said wall.

20. The intraluminal device as claimed in claim 19 wherein said control is adapted to temporally adjust an amount of force exerted by said wall.

21. The intraluminal device as claimed in claim 13 wherein said fixation system includes a tissue ingrowth portion of said body that is adapted to facilitate tissue ingrowth.

22. The intraluminal device as claimed in claim 21 wherein said plurality of anchors are adapted to resist distal migration of said body while tissue grows into said tissue ingrowth portion.

23. The intraluminal device as claimed in claim 13 wherein said wall is made at least in part of an absorbable material.

24. The intraluminal device as claimed in claim 13 wherein said anchors are distributed about said outer surface of said esophageal wall portion.

25. A method of causing at least partial satiety in a recipient having a gastro-intestinal (GI) tract comprising an esophagus, a stomach with a cardiac portion and a esophageal gastric (EG) junction having a sphincter between the esophagus and the cardiac portion of the stomach, the method comprising:

positioning a body having a wall defining a lumen in a portion of the GI tract of the recipient, said wall having at least one selected from (i) an esophageal wall portion configured to generally conform to the shape and size of the abdominal portion of the esophagus, (ii) an EG wall portion that is sized to generally conform to the size and shape of the EG junction and (iii) a cardiac wall portion that is sized to generally conform to the size and shape of the cardiac portion of the stomach;

including positioning the wall in at least one selected from (i) the esophagus (ii) the EG junction and (iii) the cardiac portion of the stomach of the recipient; and exerting force in the absence of food to the portion of the GI tract of the recipient with said wall to thereby influence a neurohormonal feedback mechanism of the recipient to cause at least partial satiety by augmenting fullness caused by food and simulating fullness in the absence of food; and fixing said wall within the portion of the GI tract with a fixation system at an outer surface of said wall that is adapted to resist distal migration of said body, said fixation system comprising a plurality of anchors comprising at least one chosen from distally directed appendages, distally directed barbs and distally directed hooks.

26. The method as claimed in claim 25 wherein said wall has said EG wall portion and said cardiac wall portion and exerting force with said cardiac wall portion at least on the cardiac portion of the stomach.

27. The method as claimed in claim 26 wherein said EG wall portion does not exert a substantial force on the EG junction of the recipient in order to allow the sphincter of the EG junction of the recipient to operate generally normally.

28. The method as claimed in claim 27 wherein said EG wall portion comprises a plurality of spaced apart tension members between the esophageal wall portion and the cardiac wall portion.

29. The method as claimed in claim 25 including exerting generally constant force with said wall on the portion of the GI tract.

30. The method as claimed in any of claim 25 including exerting an adjustable force with said wall on the portion of the GI tract.

31. The method as claimed in claim 30 including temporally adjusting an amount of force exerted by said wall on the portion of the GI tract.

32. The method as claimed in claim 25 wherein said fixation system includes a tissue ingrowth portion of said body and facilitating tissue ingrowth with said tissue ingrowth portion.

33. The method as claimed in claim 32 including resisting distal migration of said body with said plurality of anchors while tissue grows into said tissue ingrowth portion.

34. The method as claimed in claim 25 wherein said wall is made at least in part of an absorbable material.

35. The method as claimed in claim 25 wherein said positioning comprises endoscopic positioning.

36. The method as claimed in claim 35 wherein said positioning comprises expanding the body from a compressed state from a tube that is sized and shaped to pass through the recipient's esophagus.

37. The method as claimed in claim 25 wherein said anchors are distributed about said outer surface of said esophageal wall portion.

38. A method of causing at least partial satiety in a recipient having a gastro-intestinal (GI) tract comprising an esophagus, a stomach with a cardiac portion and a esophageal gastric (EG) junction having a sphincter between the esophagus and the cardiac portion of the stomach, the method comprising:

positioning a body having a wall defining a lumen in a portion of the GI tract of the recipient, said wall having at least one selected from (i) an esophageal wall portion configured to generally conform to the shape and size of the abdominal portion of the esophagus (ii) an EG wall portion that is sized to generally conform to the size and shape of the EG junction and (iii) a cardiac wall portion that is sized to generally conform to the size and shape of the cardiac portion of the stomach;

including positioning the wall in at least one selected from (i) the esophagus (ii) the EG junction and (iii) the cardiac portion of the stomach of the recipient;

exerting force in the absence of food to the portion of the GI tract of the recipient with said wall to thereby influence a neurohormonal feedback mechanism of the recipient to cause at least partial satiety in the absence of food; and fixing said wall within the portion of the GI tract with a fixation system at an outer surface of said wall that is adapted to resist distal migration of said body, said fixation system comprising a plurality of anchors that are configured to provide less resistance to proximal movement of said body than to distal movement of said body.

39. The method as claimed in claim 38 wherein said wall further has said EG wall portion and said cardiac wall portion and exerting force with said cardiac wall portion at least on the cardiac portion of the stomach.

40. The method as claimed in claim 39 wherein said EG wall portion is does not exert a substantial force on the EG junction of the recipient in order to allow the sphincter of the EG junction of the recipient to operate generally normally.

41. The method as claimed in claim 40 wherein said EG wall portion comprises a plurality of spaced apart tension members between the esophageal wall portion and the cardiac wall portion.

42. The method as claimed in claim 38 including exerting generally constant force with said wall on the portion of the GI tract.

43. The method as claimed in any of claim 38 including exerting an adjustable force with said wall on the portion of the GI tract.

44. The method as claimed in claim 43 including temporally adjusting an amount of force exerted by said wall on the portion of the GI tract.

45. The method as claimed in claim 38 wherein said fixation system includes a tissue ingrowth portion of said body and facilitating tissue ingrowth with said tissue ingrowth portion.

46. The method as claimed in claim 45 including resisting distal migration of said body with said plurality of anchors while tissue grows into said tissue ingrowth portion.

47. The method as claimed in claim 38 wherein said wall is made at least in part of an absorbable material.

48. The method as claimed in claim 38 wherein said positioning comprises endoscopic positioning.

49. The method as claimed in claim 48 wherein said positioning comprises expanding the body from a compressed state from a tube that is sized and shaped to pass through the recipient's esophagus.

50. The method claimed in claim 38 wherein said anchors are distributed about said outer surface of said esophageal wall portion.

\* \* \* \* \*